(12) United States Patent
Xu et al.

(10) Patent No.: US 11,791,044 B2
(45) Date of Patent: Oct. 17, 2023

(54) SYSTEM FOR GENERATING MEDICAL REPORTS FOR IMAGING STUDIES

(71) Applicant: RedNova Innovations, Inc., Irvine, CA (US)

(72) Inventors: Shiping Xu, Irvine, CA (US); Jean-Paul Dym, Irvine, CA (US); Yuan Liang, Los Angeles, CA (US)

(73) Assignee: RedNova Innovations, Inc., Irvine, CA (US)

( * ) Notice: Subject to any disclaimer, the term of this patent is extended or adjusted under 35 U.S.C. 154(b) by 317 days.

(21) Appl. No.: 17/006,590

(22) Filed: Aug. 28, 2020

(65) Prior Publication Data

US 2021/0074427 A1    Mar. 11, 2021

Related U.S. Application Data

(60) Provisional application No. 62/897,133, filed on Sep. 6, 2019.

(51) Int. Cl.
| | | |
|---|---|---|
| *G16H 50/00* | (2018.01) | |
| *G16H 50/20* | (2018.01) | |
| *G16H 10/60* | (2018.01) | |
| *G16H 30/00* | (2018.01) | |
| *G06T 7/00* | (2017.01) | |

(Continued)

(52) U.S. Cl.
CPC .............. *G16H 50/20* (2018.01); *G06F 40/58* (2020.01); *G06T 7/0012* (2013.01); *G06T 7/11* (2017.01); *G16H 10/60* (2018.01); *G16H 15/00* (2018.01); *G16H 30/00* (2018.01); *G06T 2207/30004* (2013.01)

(58) Field of Classification Search
CPC ........ G16H 50/20; G16H 10/60; G16H 15/00; G16H 30/00; G06T 7/11; G06T 7/0012; G06T 2207/30004; G06F 40/58
See application file for complete search history.

(56) References Cited

U.S. PATENT DOCUMENTS

| | | |
|---|---|---|
| 10,382,442 B2 | 8/2019 | Vendrell et al. |
| 11,622,818 B2* | 4/2023 | Siemionow ............ A61B 34/10 600/408 |

(Continued)

FOREIGN PATENT DOCUMENTS

WO    WO 2005/096226    10/2005

*Primary Examiner* — Khai M Nguyen
(74) *Attorney, Agent, or Firm* — Quarles & Brady LLP

(57) ABSTRACT

A software system for assisting a physician's diagnosis and reporting based on medical imaging includes software tools for pre-processing medical images, collecting findings, and automatically generating medical reports. A pre-processing software component generates an anatomical segmentation and/or computer-aided diagnosis based on an analysis of a medical image. A finding collecting software component displays the image, and facilitates rapid and efficient entry of associated findings by displaying a filtered list of templates associated with a selected region of the image and/or a computer-aided diagnosis. When the physician selects a template from the filtered list, the template may be displayed with entry options pre-filled based, e.g., on any computer-aided diagnosis. After the physician edits and/or confirms the entries, a report generation component uses the entries to generate a medical report.

28 Claims, 14 Drawing Sheets

(51) Int. Cl.
*G06T 7/11* (2017.01)
*G06F 40/58* (2020.01)
*G16H 15/00* (2018.01)

(56) References Cited

U.S. PATENT DOCUMENTS

| | | | |
|---|---|---|---|
| 2010/0114597 A1* | 5/2010 | Shreiber | G16H 10/60 |
| | | | 382/128 |
| 2011/0058720 A1* | 3/2011 | Lu | G06T 7/12 |
| | | | 382/128 |
| 2012/0035963 A1* | 2/2012 | Qian | G16H 30/20 |
| | | | 705/3 |
| 2012/0134544 A1* | 5/2012 | Long | A61B 6/508 |
| | | | 382/110 |
| 2018/0091511 A1* | 3/2018 | Vendrell | H04L 63/10 |
| 2018/0330495 A1 | 11/2018 | Jeraj et al. | |
| 2020/0020107 A1* | 1/2020 | Kakrania | G06T 3/0093 |
| 2022/0084267 A1* | 3/2022 | Ezhov | G06V 10/82 |

\* cited by examiner

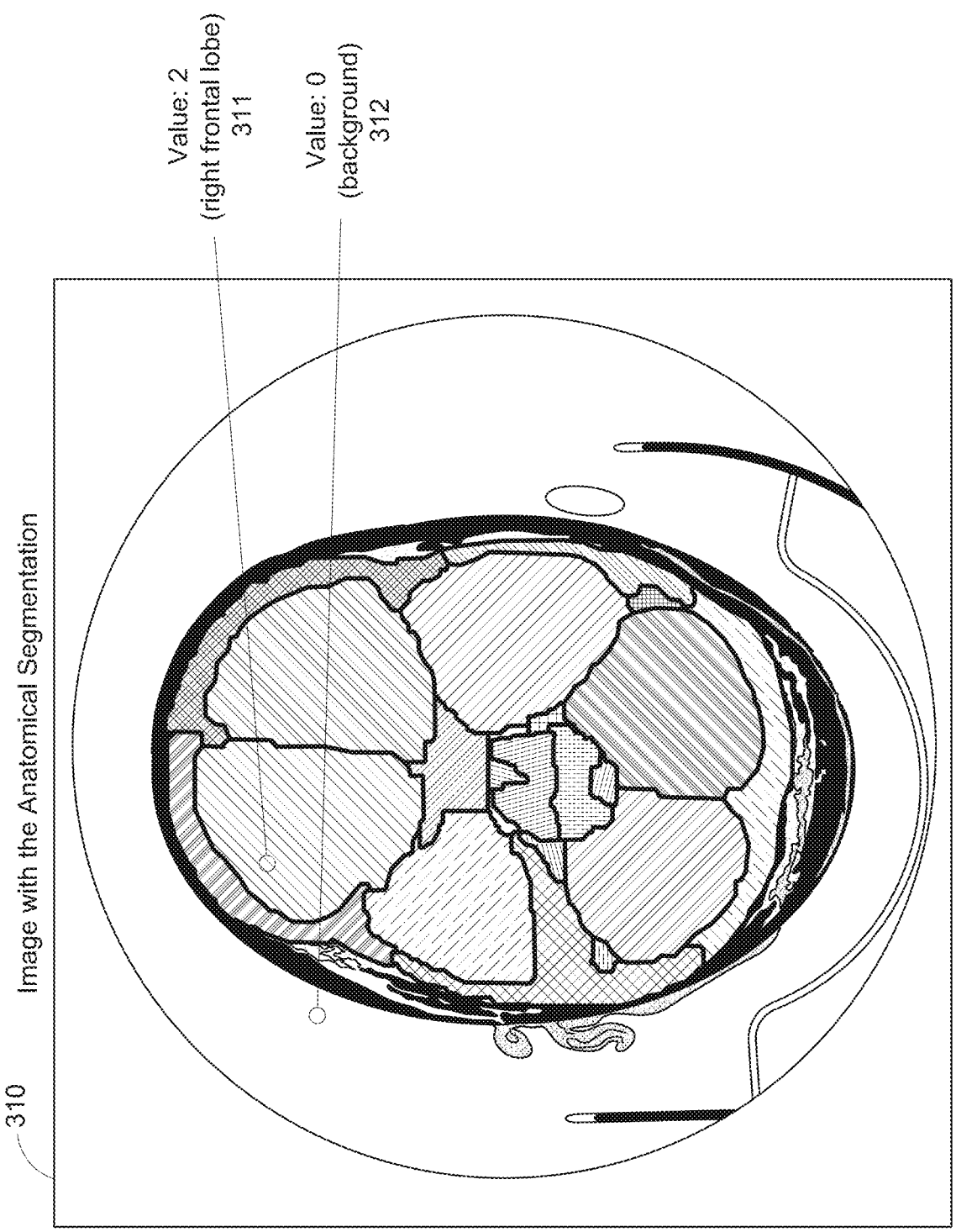
FIG. 3 (Con'd)

*600*

```
○ ○ ○                Template Num: 002

1 Selected Anatomy          [ 1 right frontal lobe  ▼ ]

2 Finding                   [ 1 parenchymal bleed   ▼ ]

3 Size —610                 [ 2 medium              ▼ ]

620—[ 12.1 ]  [ 3.4 ]  [      ] mm

4 Number of Foci —630       [ 2 2                   ▼ ]

5 Acuity                    [ 1 ----                ▼ ]

6 With Edema —640           [ 2 yes                 ▼ ]

7 Mass Effect               ☐ 1 midline shit
                                ☐ 2 local 8 Impression                ● 1 yes
                                ○ 2 no

[ Confirm ]      [ Close ]         [ Clear ]
```

Report

Exam
CT Head without intravenous contrast

Clinical History
54 years old, male;
Signs and symptoms: altered mental status/memory loss;
Additional info: Trauma

Technique
Axial computed tomography images of the head/brain without intravenous contrast. All CT scans at this facility use one or more dose reduction techniques, viz: automated exposure control; ma/kV adjustment per patient size (including targeted exams where dose is matched to indication; i.e. head); or iterative reconstruction technique..

Comparison
No relevant prior studies available.

Brain
2 acute parenchymal hemorrhages with surrounding edema in the right frontal lobe. The largest measures 1.2 (length) *0.9 (width) mm. ([5,6])

Ventricles
Unremarkable.

Bones/Joints
Unremarkable. No acute fracture.

Soft Tissues
Unremarkable.

Sinuses
The visualized paranasal sinuses are ckear.

Air Cells Mastoid
Unremarkable.

Impression
Right parenchymal hemorrhages as above.

*FIG. 11*

SYSTEM FOR GENERATING MEDICAL REPORTS FOR IMAGING STUDIES

PRIORITY CLAIM

This application claims the benefit of U.S. Provisional Appl. No. 62/897,133, filed Sep. 6, 2019, the disclosure of which is hereby incorporated by reference.

TECHNICAL FIELD

The present disclosure relates to a computer system and method for creating medical reports for imaging studies and, more particularly, to interactive computer systems methods for processing medical studies, collecting diagnoses, and generating readable medical reports.

BACKGROUND

For every medical study (X-ray, CT, MRI, and etc.) performed, a physician is ordinarily required to prepare a report describing all the pertinent findings. This includes all positive findings and pertinent negative findings of the study. The act of dictating reports usually takes a large amount of physician time for each study performed. This is because the reports need to be comprehensive and accurate so that they are useful for medical management. At the same time, with the rising number of medical imaging studies, it is imperative that physicians make diagnoses based on studies efficiently and accurately. In particular, the utilization of radiology has inversely increased, as reimbursement per each radiology study has continued to decrease. Physicians typically have to read and report as fast as possible, which has led to their stress, burnout, and ultimately, medical error. Thus, reducing the time needed to prepare a report is desirable.

A number of software tools are available to assist physicians in generating reports from medical imaging studies. However, these tools have a number of deficiencies. Some systems enable the physician to speak into a microphone. Findings are input by voice, which is converted to textual sentences automatically by software. Also, some systems enable physicians to use "macros," which are shorthand terms which are converted to phrases or sentences by the software. However, such systems can lead to fatigue, since the physician needs to speak into a microphone for 9-10 hours on a typical workday.

Another limitation of such systems is that they are vulnerable to speech interpretation accuracy. They can make mistakes when doing conversion, or even misinterpret a whole sentence. The variety of speaker accents, as well as uncommon medical terminologies spoken, also predispose these systems to error. Thus, physicians often have to repeat their words, or use the keyboard to type an alternative. This is a significant drawback because either way will cause physicians to spend extra time creating the reports. Moreover, medical errors can occur if a physician does not double check the sentences produced from speech recognition; such errors are a common cause of medical malpractice. Left/right sided errors, or general location related errors, are also an unfortunate common cause of significant medical error with these systems.

SUMMARY

A computer system and associated methods are disclosed for assisting physicians, such as radiologists, in efficiently and accurately creating medical reports. The system preferably comprises software for pre-processing medical images, collecting findings, and automatically creating reports. The system can be used in all medical imaging modalities, such as CT, MRI, etc.

In one embodiment, the system implements a semi-enhanced mode and an enhanced mode. In the semi-enhanced mode, the pre-processing software generates an anatomical segmentation of a medical image. The generated segmentations are passed to the finding collecting software of the system. The finding collecting software displays the medical image with an interactive interface. The software captures mouse clicks (and/or other types of interactions such as touch screen taps and gestures) from the physician on the location of interest, and prompts the physician to select a template to fill in for describing the finding, from a list of possible templates. The list is preferably a filtered list that consists of the templates related to the anatomies around the cursor location of activation.

When used in the enhanced mode, the software also generates a computer-aided diagnosis for the study. Different from the semi-enhanced mode, the physician is prompted with a list of templates that are related to the findings around the selected (e.g., clicked on) location according to a computer-aided diagnosis. Moreover, the templates selected are also preferably prefilled with information from the computer-aided diagnosis for saving time. The physician can edit or confirm the template with the pre-filled text.

The templates in the systems can be anatomy-finding based, such that there can be a template for each specific finding type at each anatomy. For each template, there are preferably entries and options for describing a finding, and the physician can preferably fill in the template by one or more types of human-machine interactions such as mouse clicks, screen taps, typing, speaking into a microphone, and/or dragging with a mouse or touch gesture. Once the physician finishes describing all the findings, the report generating software converts the filled templates into a medical report. The conversion is done using a predefined mapping protocol that maps template entry-option pairs to readable sentences. The allocation of findings to locations on the report is preferably determined by predefined rules.

The system may provide some or all of the following advantages: 1. reduced time to complete diagnosis, by using predefined templates for describing findings, and automatically converting filled templates into reports; 2. reduced interpretation mistakes that can occur when the physician dictates complete sentences as in the current practice, since the physician instead describes findings mainly by making selections based on the aforementioned options provided via templates; 3. the system is inherently adaptable for multiple language interchange, e.g. an imaging study report is generated in one language and viewed in another language; this is because the system preferably uses built-in entries and options for describing findings, which are stored with encodings that are independent of languages; 4. the system enables indexing of diagnoses by findings, because all the findings generated from the system are preferably standard in sentence format and wordings; 5. typographical and left/right errors are avoided.

The additional features and advantages will become more apparent from the following detailed description and accompanying drawings.

Neither the foregoing summary nor the following detailed description purports to define or limit the invention. The invention is defined by the claims.

BRIEF DESCRIPTION OF THE DRAWINGS

A preferred embodiment, and an example application involving a brain CT scan with a small amount of blood/hemorrhage in the right frontal lobe, will now be described with reference to the following drawings.

FIG. 6 shows an example of the interactive template generated in the enhanced mode, following the process as illustrated in FIG. 8, which is used to guide the physician to fill in descriptions of a finding.

FIG. 11 shows an example of the interactive report screen with the generated report from the example in FIG. 7, by following the process as in FIG. 9.

DETAILED DESCRIPTION OF PREFERRED EMBODIMENTS

Introduction

The invention comprises a software-based system for assisting physicians in creating diagnostic reports based on a medical study. The following detailed description illustrates the operation of the software system as applied to the diagnosis of a brain CT study with a small amount of blood/hemorrhage in the right frontal lobe. The invention is also applicable to numerous other types of medical imaging studies, such as MRI and X-ray imaging studies. In addition, the invention is applicable to medical studies of other anatomies, such as lung and breast. The following description is not intended to be limiting.

The following terminology is used in this disclosure to describe a system according to a preferred embodiment of the invention. Neither this terminology nor the associated description of the system limits the scope of the invention.

Figure 5:
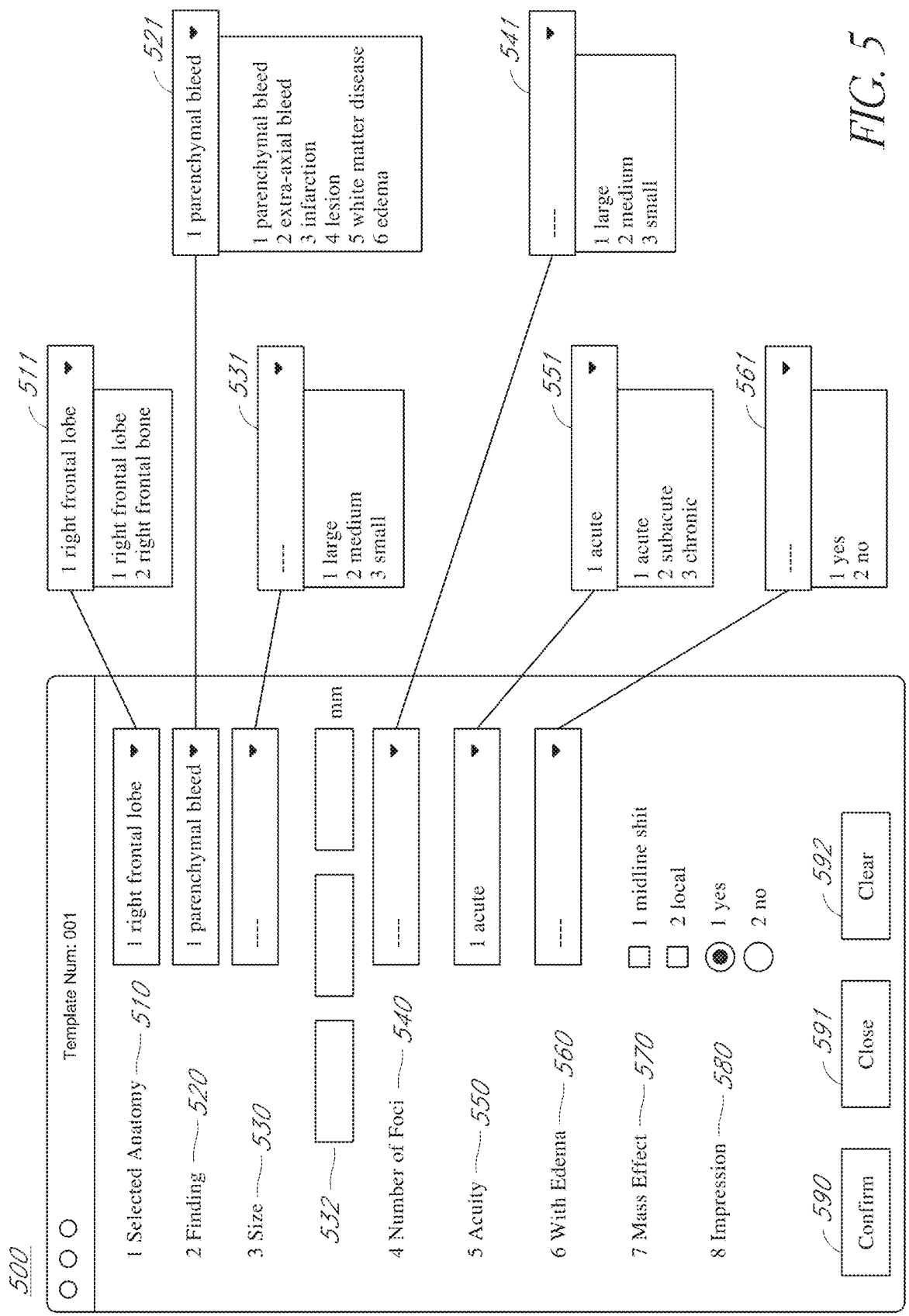
FIG. 5 shows an example of the interactive template generated in the semi-enhanced mode, following the process as illustrated in FIG. 8, which is used to guide the physician to fill in descriptions of a finding.

Template: a template refers to a pre-formatted form that serves as the starting point for describing a finding. It can include entries for detailing different aspects of a finding, and each entry can be associated with several options from which to choose. One typical template is shown in FIG. 5, where 530 shows one of the entries and 531 shows options of that entry.

Anatomical segmentation: an anatomical segmentation refers to the separation of anatomical structures from background or from each other. Each pixel of a medical image can be labeled by one anatomical type, and pixels of the same label can be grouped together to identify various structures. One typical anatomical segmentation is shown in 310 of FIG. 3, where 311 shows the right frontal lobe and is one of the anatomical structure.

Computer-aided diagnosis: a computer-aided diagnosis refers to the separation of locations of interest for the diagnostic purpose. Each pixel of a medical image can be labeled according to whether there is a positive finding or not. One typical computer-aided diagnosis is shown in 311 of FIG. 3, where 321 is hemorrhage and is one of the positive findings.

Figure 4A:
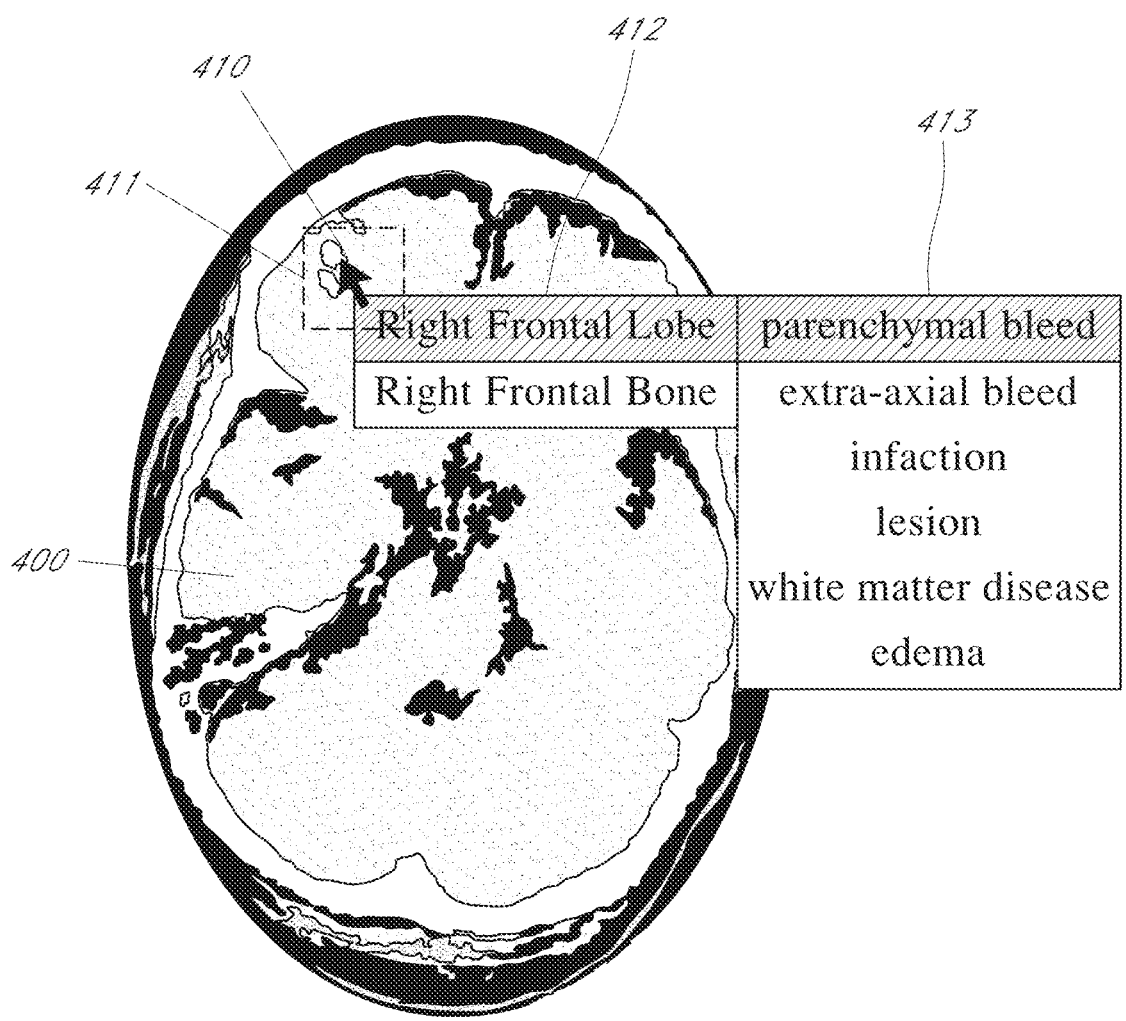
FIG. 4a shows an example of the interactive study display screen of the finding collecting tool, with its response to the physician's selections in the semi-enhanced mode.

Semi-enhanced mode: this mode refers to a working mode of the system that makes use of an anatomical segmentation of a medical image. In this mode, when entering a finding, the physician is prompted to select a template from a list of templates related to the anatomy at the location of activation. FIG. 4a shows the system working this mode, where 413 can be the template list. The physician then describes the finding by filling in the selected template.

Figure 4B:
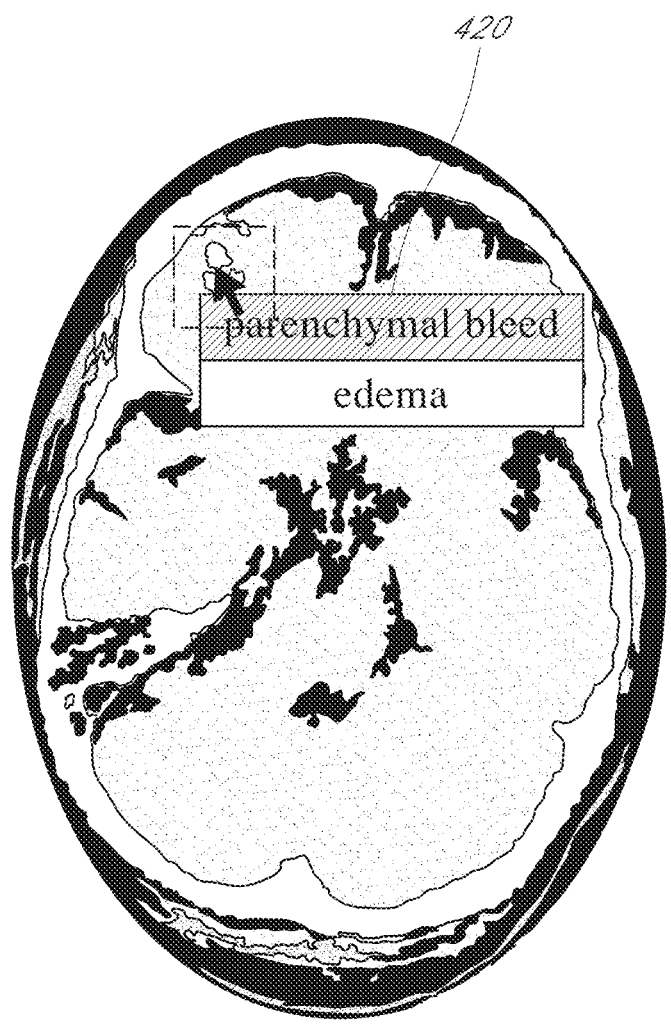
FIG. 4b shows an example of the interactive study display screen of the diagnosis software tool, with its response to the physician's selections in the enhanced mode.

Enhanced mode: this mode refers to a working mode of the system that makes use of a computer-aided diagnosis of a medical image, where the segmentation can be performed by the background computer-aided system. In this mode, when entering a finding, the physician is prompted to select a template from a list of templates that related to the findings from computer-aided diagnosis at the location of activation. FIG. 4b shows the system working in this mode, where 420 can be the template list. The template is automatically pre-filled for describing the finding according to the computer-aided diagnosis. The physician can confirm or change the findings.

System Overview and Architecture

The system includes software tools for pre-processing medical images, collecting findings, and automatically generating readable medical reports. These tools may, but need not, run on a common physical machine (e.g., workstation, local server, remote server, cloud based server); for example, in some embodiments, different components may run on different physical computers.

Figure 1:
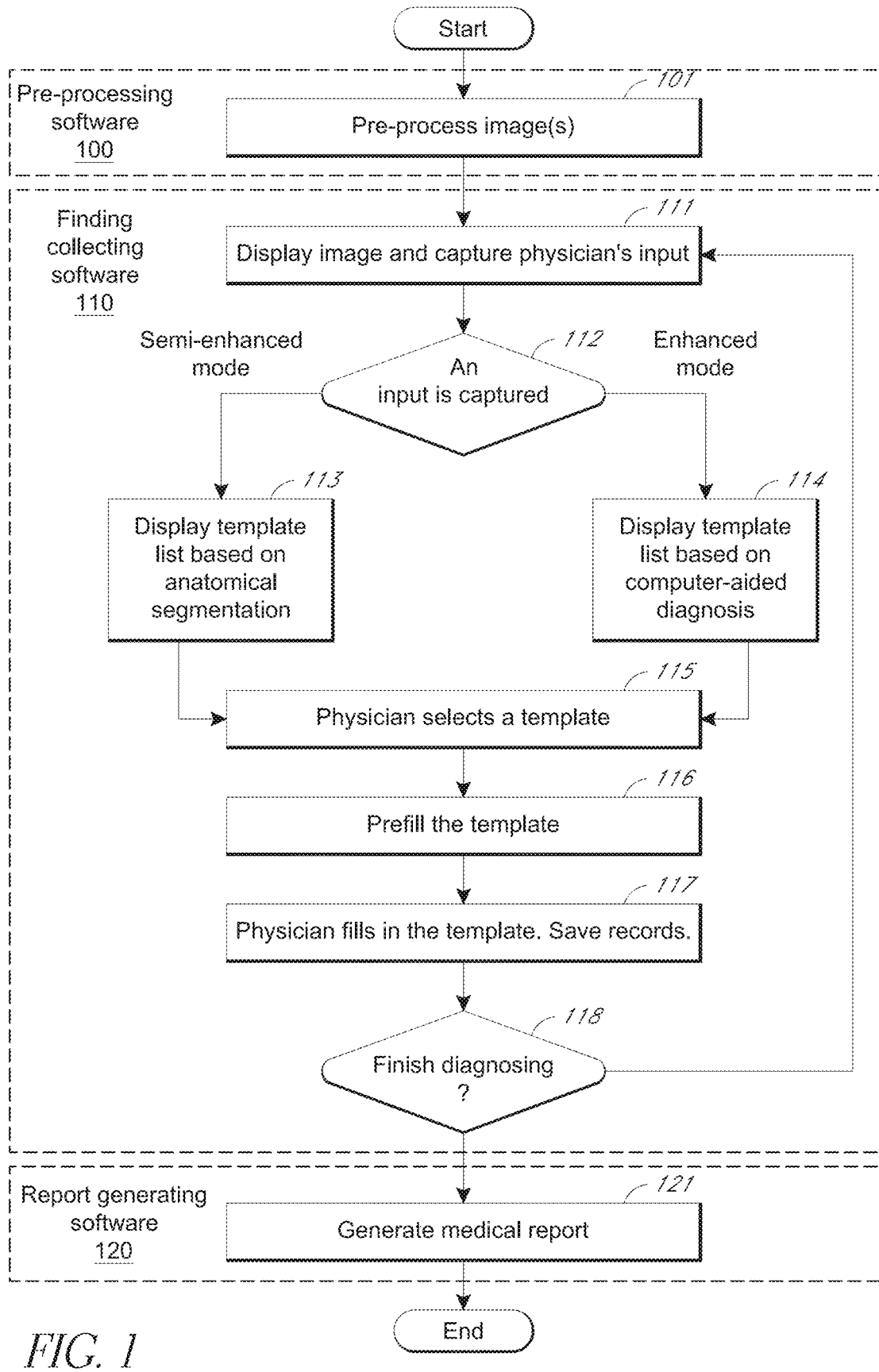
FIG. 1 is a flowchart illustrating the process flow of the system according to one embodiment.
Figure 3:
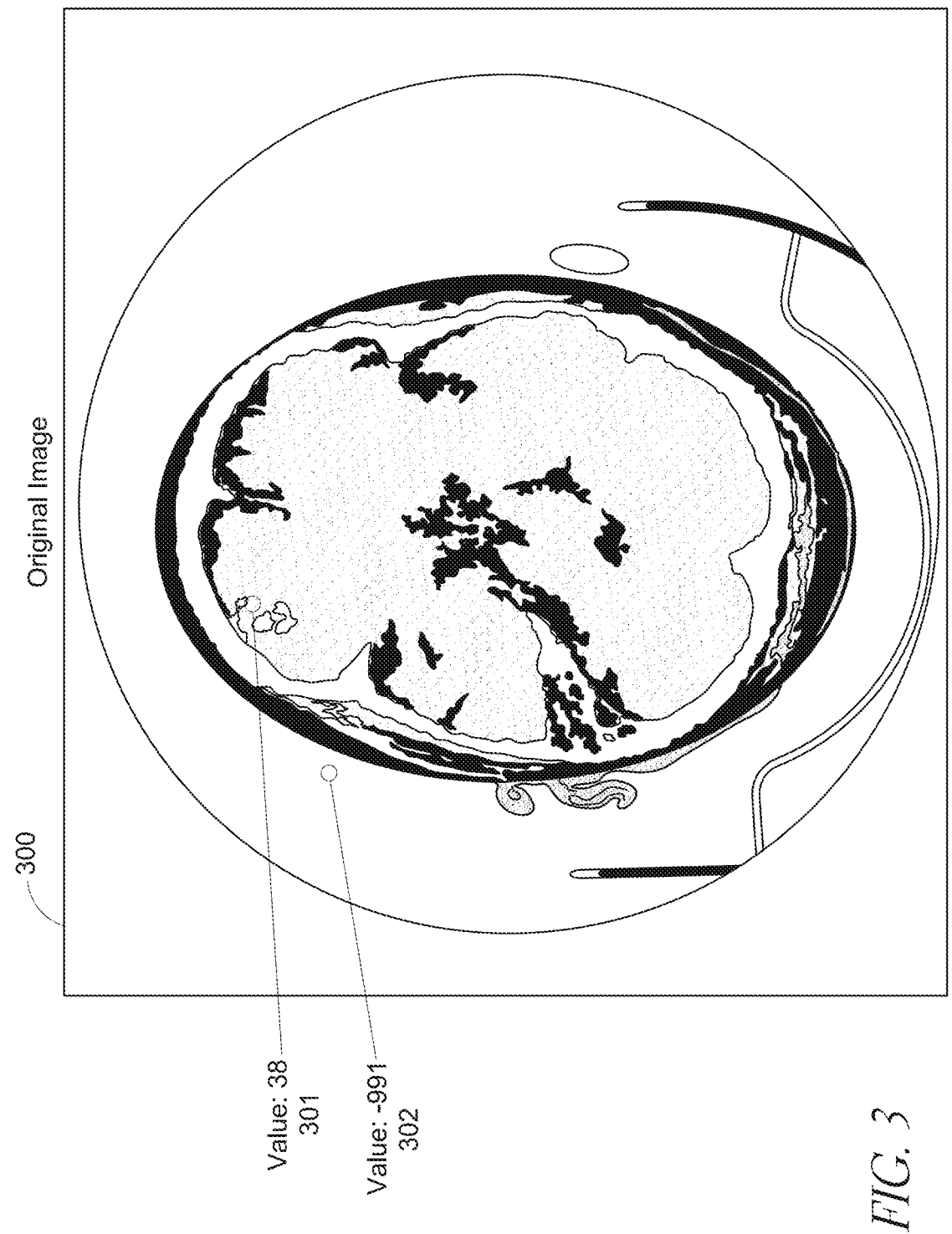
FIG. 3 shows an example of typical results from the pre-processing software tool illustrated with a brain CT image (change image enhanced) (hemorrhage, negative).
Figure 3:
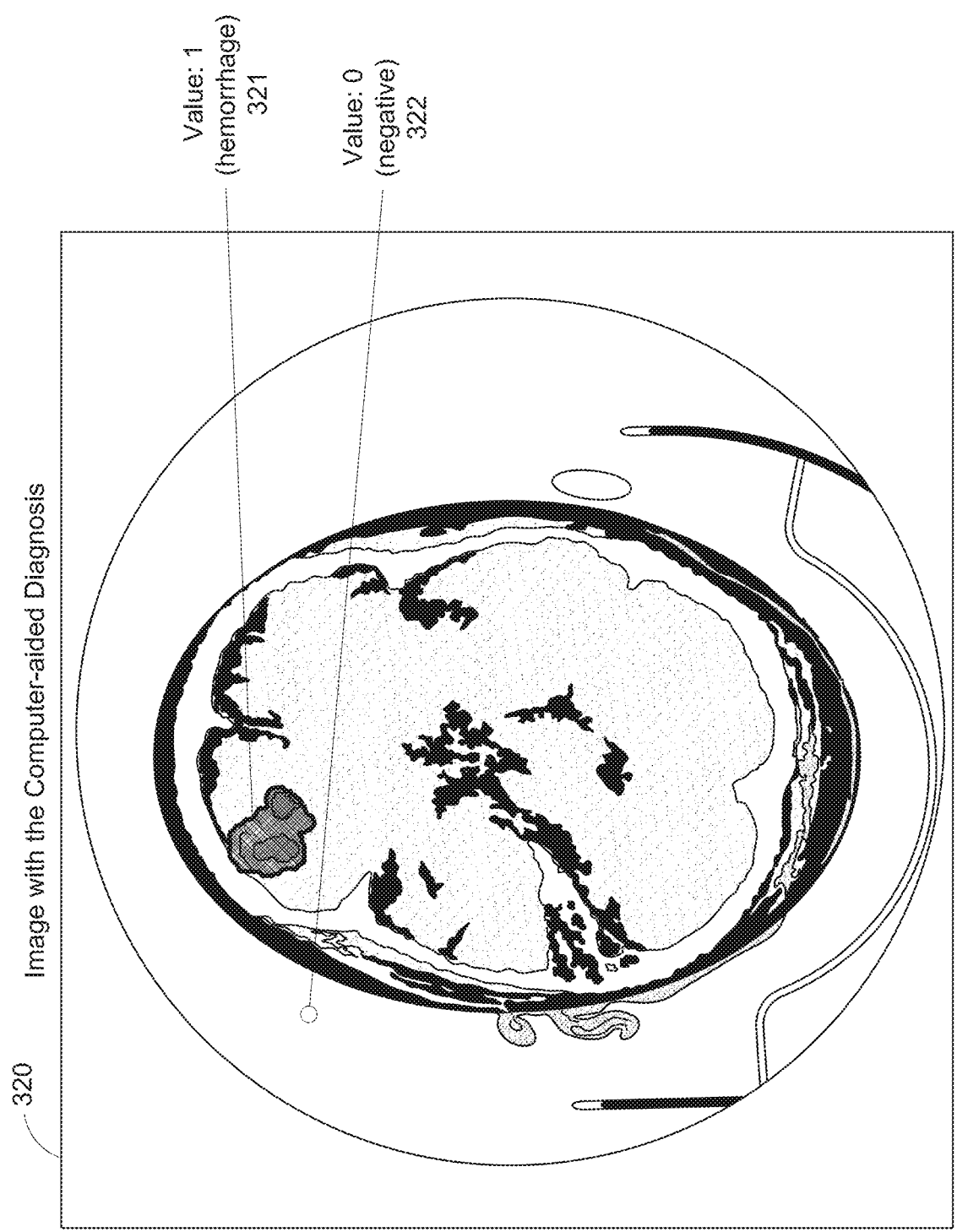

FIG. 1 illustrates the process flow of the system according to one embodiment. The pre-processing software 100 pre-processes a medical image in step 101, which generates an anatomical segmentation and/or computer-aided diagnosis. Software-based anatomical segmentation of medical images is well known in the art, and involves dividing an image into areas corresponding to organs, tissues, and/or other anatomical structures. Software for generating diagnoses from medical images is also well known, and typically (but not necessarily) involves applying trained machine learning models to predict the existence and/or locations of positive findings. An example of the generated segmentation is illustrated in FIG. 3, where 300 is the original image, and 310 and 320 show the anatomical segmentation and computer-aided diagnosis respectively. In the anatomical segmentation 310, different regions or segments of the CT image are shown in different colors.

The finding collecting software 110 interactively displays the imaging in step 111. It keeps track of the location of the cursor over the image, and captures physician's mouse clicks. (Although this description refers to mouse clicks, various other types of user interactions may additionally or alternatively be used to select image locations, such as those commonly used with touch screens and/or augmented reality, virtual reality and mixed reality devices and systems.) If a diagnosis has been generated for the image by the pre-processing software, the image may optionally be displayed with a marker or overlay that identifies the image location or region corresponding to the diagnosis.

Figure 7:
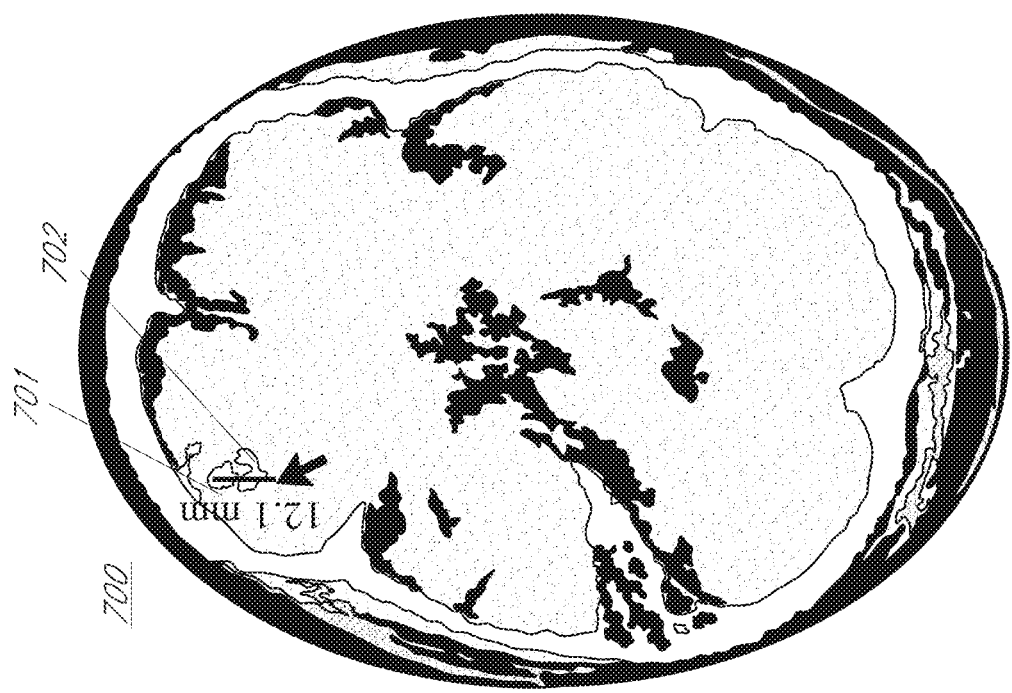
FIG. 7 shows an example of using the interactive measuring tool to rapidly fill in measurements into the current template.

When the physician clicks at the location of interest as in step 112, a drop-down menu is displayed with a filtered list of possible templates for describing the finding at the cursor's location. The templates include predefined entries and options specifically designed according to the finding type and anatomy. Examples of templates are shown in FIG. 6 and FIG. 7. In the illustrated embodiment, the list of templates presented depends on whether the system is being used in the semi-enhanced mode versus the enhanced mode. In some implementations, the physician can select between these two modes; in other implementations, the finding collecting software 110 may only implement one of these two modes.

In the semi-enhanced mode, the list contains templates related to the anatomies around the cursor's location as in step 113, as determined by referring to the anatomical segmentation. In the enhanced mode, the list contains templates related to the possible findings around the cursor's location as in step 114, as determined by referring to the computer-aided diagnosis. The physician is prompted to select one suitable template from the list as in 115. Because the template lists are filtered based on the cursor location and/or computer-based diagnosis, the physician can select a relevant template quickly and efficiently. In other implementations, the semi-enhanced and enhanced modes may be combined in to a single mode, such that the physician is concurrently presented with a list (or separate lists) of two different types of templates—some of which depend on a computer-aided diagnosis, and some which do not.

The finding collecting software 110 may generate the filtered list(s) of templates using pre-defined template classifications. Specifically, each template may be stored in computer memory in association with (1) one or more anatomy identifiers, and/or (2) one or more diagnosis identifiers. To generate the filtered list in the semi-enhanced mode, the system may identify and select, from a master set of templates, all templates having an anatomy identifier that matches the anatomy classification of the currently selected image location.

To generate the filtered list in the enhanced mode, the system may identify and select, from the master set of templates, all templates having a diagnosis classification that matches a diagnosis classification, if any, generated by the pre-processing software 100 for the currently selected region or segment of the image. (In some embodiments this filtered list may alternatively include all templates corresponding to any computer-aided diagnosis generated for the image, such that the filtered list is not specific to any particular region of the image.) In some cases, multiple computer-aided diagnoses may have been generated for the currently selected region, in which case the filtered list may include different templates for different types of diagnoses.

In step 116, before displaying the selected template, it is first prefilled according to the physician's preset preferences (if any), and/or based on any computer-aided diagnosis. The physician can then edit the template in step 117 by making selections, typing and/or speaking into a microphone. Steps 111-117 are repeated until the physician describes all the findings in the image. The physician may indicate completion of the diagnosis task in step 118 by, for example, selecting an associated user interface element. Then, the report generating software 120 collects all the filled templates, and automatically converts them into a medical report, as in step 121. The physician can then edit, or confirm, the report. Ordinarily, the quantity of text included in the written report significantly exceeds the quantity of text, if any, entered by the physician into the template or templates; thus, the data entry burden on the physician is significantly reduced.

For studies that involve multiple medical images, all images are pre-processed for anatomical segmentation and/or diagnosis in step 116. Any predicted anatomical structure and diagnosis may be shown in one or multiple images. Upon entering the description of a finding, the physician may invoke the corresponding template from any image in step 111. The description of the finding may be filled in by using one template. The physician may repeat steps 111-117 for describing all findings from all images. Upon confirming the completion of the diagnosis, one medical report containing all findings for the study is generated in step 121.

When the system is used in the enhanced mode to analyze a multi-image study, the pre-processing software may arrange the multiple images in a viewing queue such that (1) images with positive findings (detected or predicted abnormalities) are displayed before images with no positive findings, and (2) images with more severe positive findings are displayed before images with less severe positive findings. This further improves physician efficiency by reducing the need for the physician to go back to previously viewed images when entering findings.

Figure 2:
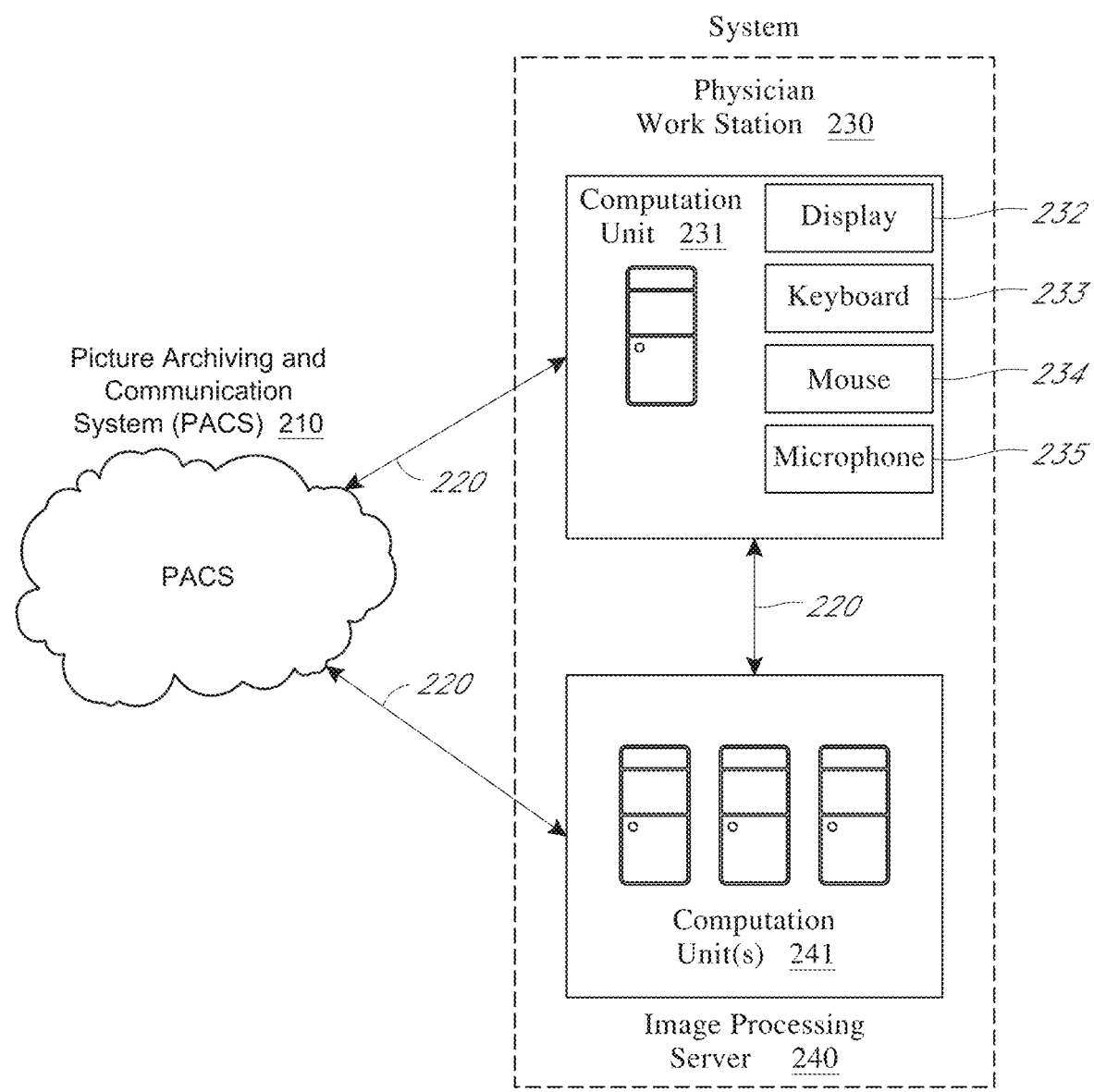
FIG. 2 is a block diagram illustrating an example of a computer system configuration for the present invention.

FIG. 2 illustrates one example of a computer system configuration that may be used to implement the present invention. Picture Archiving and Communication System (PACS) 210 is a repository that stores medical images from healthcare providers. The system can include a Physician Work Station (PWS) 230, and an optional Image Processing Server (IPS) 240. The illustrated IPS consists of computation units 241 capable of performing image processing tasks with a high degree of performance. Each computation unit typically includes a hardware processor coupled to a memory that stores program instructions executed by the hardware processor. In embodiments that include an IPS, the PWS preferably runs the finding collecting software and report generating software, while the IPS runs the pre-processing software. Otherwise, the PWS runs all three components. An example PWS includes a computation unit 231, which interconnects with various components including a display 232, a keyboard 233, a mouse 234, and a microphone 235. The microphone is optional, and can be used to collect users' speech as an additional method of input to the system. The PWS can additionally or alternatively include other types of user input devices, such as a touch screen, an eye tracking device, or an augmented reality headset. An example IPS is equipped with 4 Nvidia Titan Xp 12G GPU cards, and an Intel i9-7960X CPU. The logical connections 220 between the PACS, PWS, and IPS can be based on the Ethernet, Wide Area Network (WAN), Local Area Network (LAN), and/or wireless network technologies.

In some embodiments, the system's user interface may be a browser-based interface in which the user interacts with the system's software components using a conventional web browser. In such embodiments, the pre-processing software 100, finding collecting software 110 and/or report generating software 120 may run remotely from the physician on a server system, such as a cloud based server system. The physician-user in such embodiments may interact with the system via a client device, such as a workstation or tablet, that runs a browser program. Web pages loaded by the browser may include scripts, such as Javascript scripts, that implement the user interface functions described herein (such as the ability to select image portions, take measurements, etc.).

Pre-Processing Software

The pre-processing software 100 (FIG. 1) generates anatomical segmentations and/or computer-aided diagnoses for the image with computer vision algorithms. Referring to FIG. 3, an example of pre-processing results is illustrated with a brain CT image. An axial plane of the original brain CT without any processing is shown as 300, where the intensity of each pixel is determined when the image is captured. Two typical pixels, shown as 301 and 302, have the intensity values of 98 and −991 respectively. The anatomical segmentation generated from the pre-processing software is shown as 310, where it is displayed as a mask over the original image. Different values in the mask represent different anatomical labels of each pixel, and are displayed in different colors for the ease of illustration. The pixels 311 and 312 have label values of 2 and 0, where in the example represent for the right frontal lobe and the background, respectively. A computer-aided diagnosis generated from the pre-processing software is shown as 320, where it is displayed as a mask over the original study. Different values in the mask represent different types of findings in the study, and are shown with different colors. The pixels 321 and 322 are given label values of 1 and 0, representing (in this example) the hemorrhagic bleed and a negative finding, respectively.

The pre-processing software may use computer vision algorithms that are known in the art. Examples of such algorithms are described, e.g., in Ronneberger, O.; Fischer, P.; and Brox, T. 2015. U-net: "Convolutional networks for biomedical image segmentation," In International Conference on Medical image computing and computer-assisted intervention, 234-241, Springer; and Yuan Liang, Weinan Song, J. P. Dym, Kun Wang, Lei He, "CompareNet: Anatomical Segmentation Network with Deep Non-local Label Fusion", MICCAI 2019, the disclosures of which are hereby incorporated by reference.

Finding Collecting Software

In a preferred embodiment, the finding collecting software 110 (FIG. 1) displays the medical image, and interactively collects findings from the physician. As explained above, there are two modes for collecting a finding. The semi-enhanced mode takes advantages of the anatomical segmentation from the pre-processing software. It provides the physician with a list of possible templates for describing a finding when he or she clicks on a location of interest. Differently, in the enhanced mode, the physician is provided with a list of templates for possible findings around the selected image location according to the computer-aided diagnosis or diagnoses. The templates can be pre-filled based on the relevant computer-aided diagnosis, which further reduces the time needed to enter a finding.

FIG. 4a shows an example of collecting findings in the semi-enhanced mode. The software displays an axial plane of the image as 400. The physician starts entering a finding by moving the cursor to the location of the interest and clicking a predefined key as 410. The software detects the location of the cursor on the image, and collects the anatomies existing within a range of distance 411 from the cursor in the anatomical segmentation. The range of distance 411, referred to as the bounding box, can be defined by the user as a preset configuration parameter. The interface screen then shows a dropdown menu 412 at the cursor, which lists all the anatomies collected. The order of the list can be determined by the distance of the anatomy from the cursor location at triggering, from the nearest to the farthest. The physician selects one of the anatomies from 412, and then is presented with a submenu 413, which contains all types of findings that are associated with the selected anatomy. Each such finding may correspond to a different respective template. Once a suitable finding type is selected by the physician, the software shows the corresponding template for the selected anatomy-finding type. In this example, the right frontal lobe is the selected anatomy, and the parenchymal bleed is the selected finding type. Thus, the predefined template for right frontal lobe—parenchymal will be shown.

FIG. 4b shows an example of collecting findings in the enhanced mode. Similarly, the physician starts entering a finding by moving the cursor to the location of interest and clicking a predefined key. (In some embodiments the location of interest may be pre-selected by the finding collecting software component based on the computer-aided diagnosis, in which case the cursor may be pre-positioned over that region but movable by the physician.) The software collects all findings from the computer-aided diagnosis that are within the bounding box centered by the cursor location. Then, a drop-down menu 420 is displayed which contains a list of findings generated by the computer-aided diagnosis routines. The user can select a suitable finding type, and the software shows the corresponding template for that finding type. Different from the semi-enhanced mode, the template shown can be pre-filled according to the information from the computer-aided diagnosis. In this example, the parenchymal bleed is selected from the list, and the software will show the template for this finding type.

FIG. 5 illustrates an example of a template triggered in the semi-enhanced mode. The entries in a template are designed for collecting descriptions of the selected finding. The entries can be associated with predefined options in the format of, e.g., a dropdown menu, radio button, and/or checkbox, for the physician to select from. In the example, 510, 520, 530, 540, 550, 560, 570, 580 are entries of this category, and 511, 521, 531, 541, 551, 561, 571, 581 show their options, respectively. Some of the entries, e.g. 550 and 580 in the example, can be prefilled according to the presets of the physician. The text boxes are for entries that cannot practically be described with preset options. For example, 532 is the entry for describing the measurements of the finding, which should be filled in with the exact numbers according to the individual finding. The physician can click on (1) the "confirm" button 590 when finished filling the template and close the window, (2) the close button 591 to close the window without saving, or (3) the clear button 592 to clear all the filled fields on the template. For the input method, the physician can use a keyboard or speak into a microphone as alternatives to a mouse. As an example of using a keyboard, the menu of 530 expands if the "3" key is pressed. Then if the key of number 2 is pressed, the medium option can be selected. As an example of using a microphone, when THREE is pronounced, the size option 530 expands its menu. Then if the word TWO is pronounced, the medium option on 531 is selected. In embodiments that use eye tracking or head pose tracking, the physician can alternatively make the selection by, e.g., looking at the desired entry or option for a threshold period of time (e.g., 2 seconds), or by looking at the desired entry or option while performing an additional action. In some embodiments, the physician may be able to select an entry or option by pointing a wireless, handheld pointer device at the desired screen location and then depressing a button on that device.

FIG. 6 illustrates a template triggered from the enhanced mode as an example. The template window 600 is pre-filled based on the computer-aided diagnosis generated by the pre-processing software. In this example, by referring to the computer-aided diagnosis as in 320 (FIG. 3), the measurement options 620 are pre-filled by the system by computing the number of pixels with the parenchymal bleed label and the pixel thickness. The Size option 610 is pre-filled with medium, by comparing the measurements with predefined thresholds for size levels. The Number of Foci option 630 is pre-filled with 2, because two separate clusters of bleed are detected from the diagnosis. The With Edema option 640 is pre-filled to "yes," because edema labels are found near the finding in the diagnostic segmentation. The physician can edit any entries or confirm the template.

When the physician uses the cursor to measure a finding, the length measurements can be automatically entered into the appropriate text box in the template. This saves time in comparison to typing the values with a keyboard. Referring to FIG. 7 for an example, with the measuring function activated, the physician can move the cursor over the study 700 to measure a finding. A straight line 702 shows its trajectory, and the number shows 701 measured length. With the template 710 displayed, the measurement 12.1 mm will be automatically filled into the blank measurement option 711.

Figure 8:
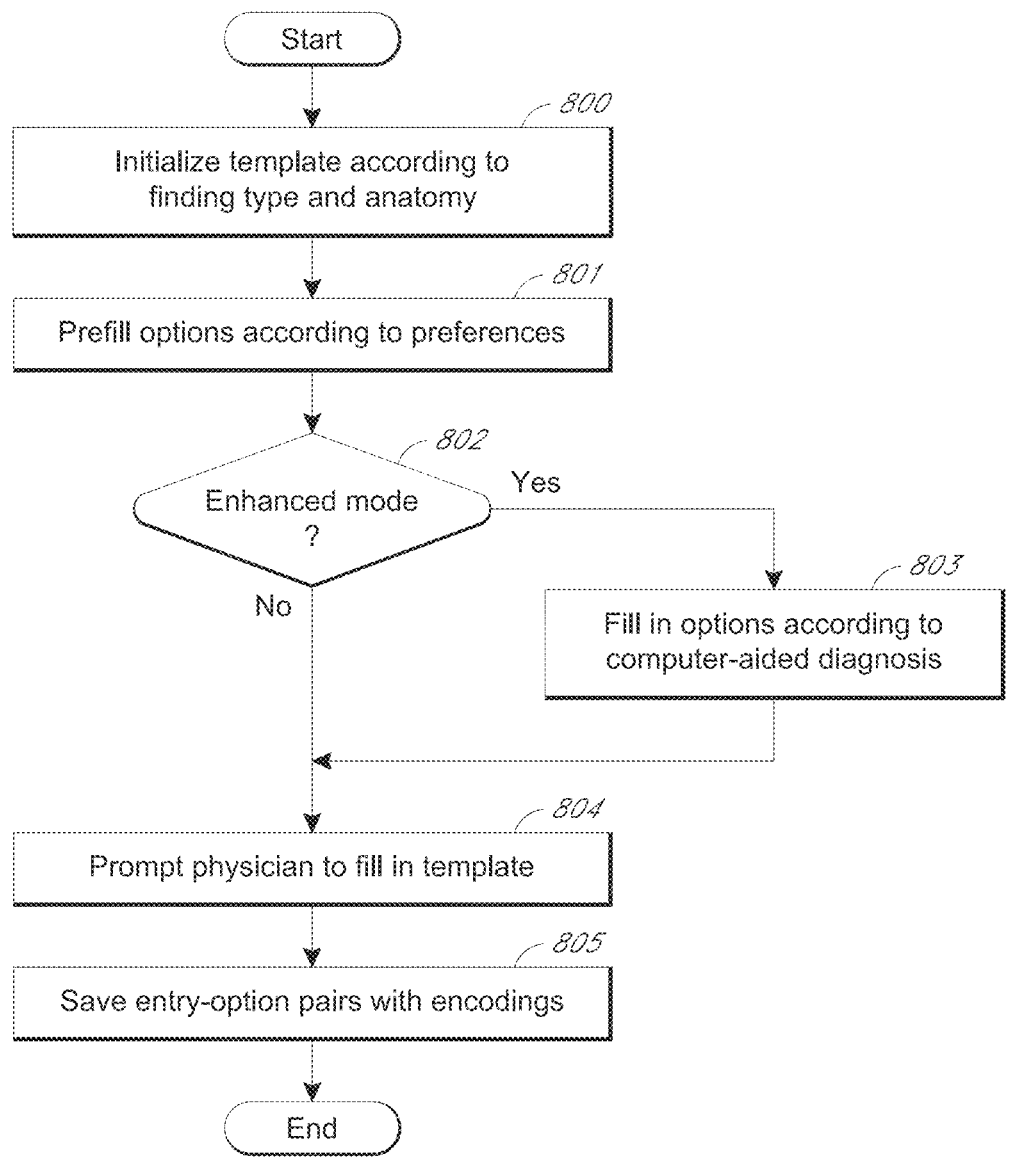
FIG. 8 is a flowchart illustrating the process flow of generating a pre-filled template based upon the physician input as made in FIG. 4a and FIG. 4b.

Referring to FIG. 8, a flowchart illustrates a template processing method implemented by the finding collecting software 110. The software first initializes a certain template according to the physician's selection in step 800. Then some options in the template may automatically be prefilled according to the presets of the user in step 801. In step 802, the software determines if the template is triggered in the enhanced mode. If true, then in step 803, more options in the template are prefilled by referring to the associated computer-aided diagnosis. For example, the measurements options 630 (FIG. 6) are filled with 12.1 and 3.4, which can be measured by the software using the number of pixels in the image with the parenchymal bleed label, and the pixel thickness of the image. As in step 804, the physician is prompted to fill in or edit the template by, e.g., using mouse clicks, typing on a keyboard, and/or speaking into a microphone. After the physician confirms the template, the template is saved in 805.

All the entries and selected options are stored as entry-option pairs with encodings that are independent of the language used for the diagnosis. The entry-option pairs are structured and standard, and can be encoded (e.g., 010001 for one entry-option pair and 10001 for another pair) for storage and for comparison. Therefore, the system can easily compare findings by different physicians or by computer-aided diagnosis algorithms, regardless of the spoken languages used by the physicians and in the reports. By comparison with the accurate finding either by experts or by algorithms, the quality of a finding by a physician or an algorithm can be measured or scored for the purpose of training, quality measurement, or certification. The encodings, along with the report generating method as explained in the next section, enables the multiple language interchange, e.g. the system can convert the collection of entry-option pair for a given image study directly into a medical report in any of a variety of languages (English, Chinese, French, Spanish, etc.) supported by the system.

Report Generating Software

Figure 9:
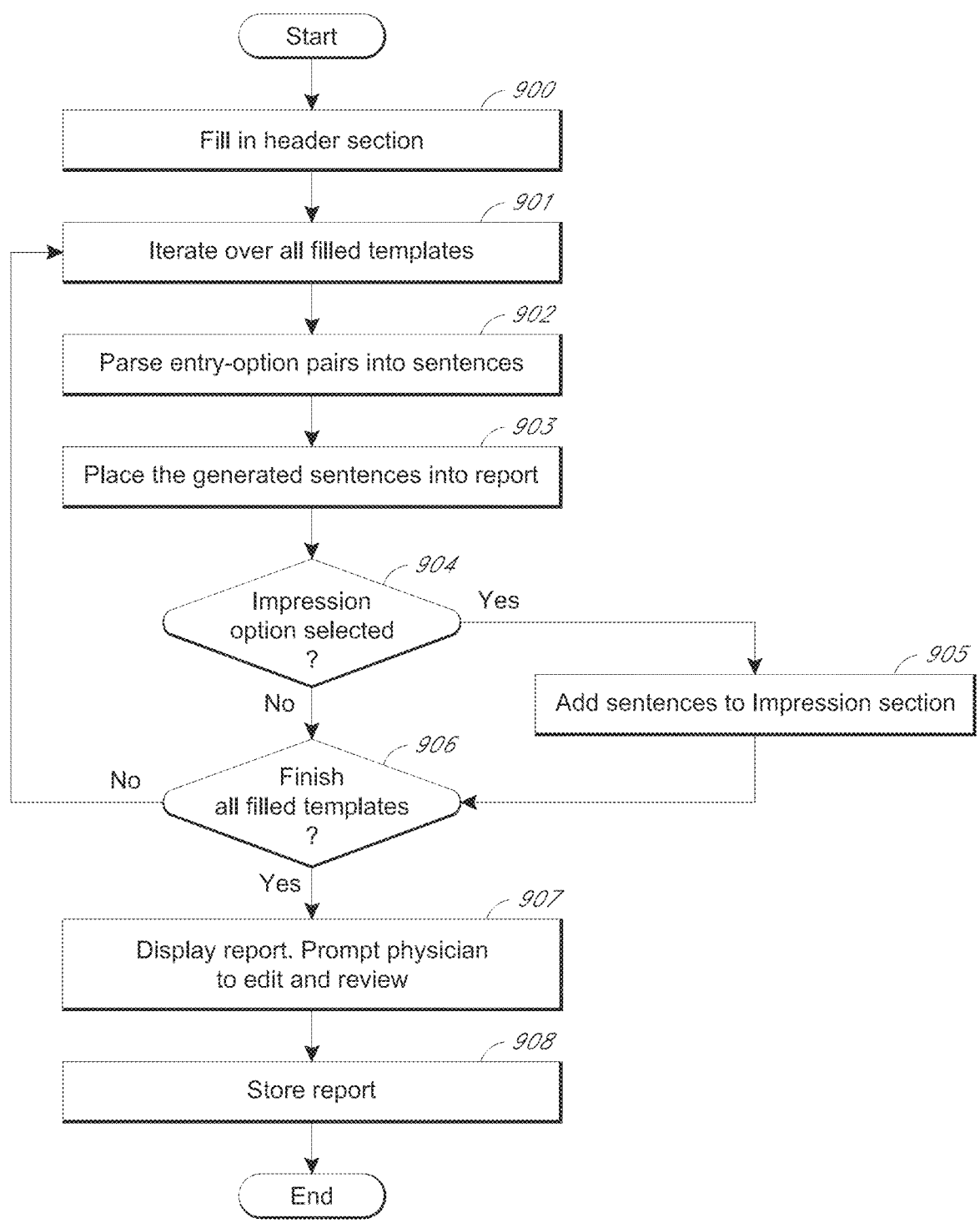
FIG. 9 is a flowchart illustrating the process flow of automatically generating a medical report from the filled templates.

Referring to FIG. 9, the flowchart illustrates the process flow of the report generating software, which automatically generates a readable report from all templates filled for the study. One example of the generated report is shown in FIG. 11. When the physician confirms that all of the findings have been described with templates, the software first generates the header section in step 900, which include Exam Name, Clinical History of the patient, Technique used for screening, and Comparison studies. All the information can be drawn from the meta-data of the image. The report generating software then iterates through all the filled templates of the image in step 901. For each template, entry-option pairs are converted into sentences (step 902), and placed into the corresponding position of the report (step 903) according to a predefined protocol or format. The conversion and placing methods are illustrated with more detail below. If the template has the impression option set to "yes" (step 904), the parsed template will also be added to the impression part of the report (step 905), as shown in 1120 (FIG. 11). The software then checks if all the filled templates have been parsed in step 906, and displays the generated report in an interactive window in step 907. The user can edit or confirm the report, and the report is stored (step 908).

Figure 10:
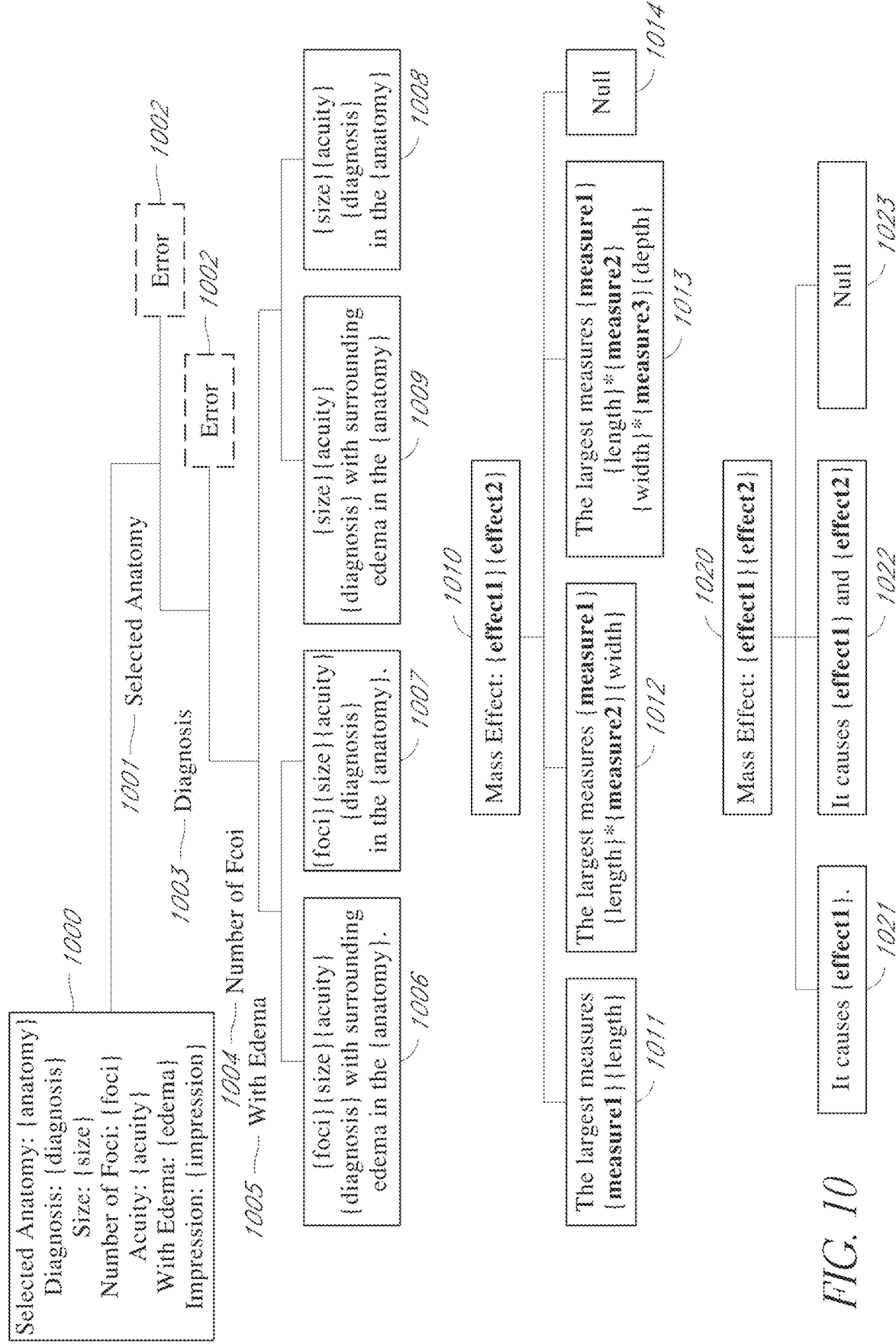
FIG. 10 shows an example of the report generating software parsing/converting a filled template into sentences.

Referring to FIG. 10, the block diagram illustrates the method for automatically parsing a filled template into readable sentences by using one example. All the entry-option pairs are collected from a filled parenchymal template as shown in FIG. 5 and FIG. 6. Three sentences are generated for the template from entry-option pair groups 1000, 1010, and 1020, respectively. Note that the entry-option pairs are presented in bold within brackets, and a None value for an entry-option pair means no option is selected for that entry from the template. For the group 1000, if the Anatomy entry 1001 or Finding entry 1003 is has no option selected, there will be an error, because both entries are necessary for describing a finding. Then, depending on whether there are any values for Number of Foci 1004 and With Edema 1005, the generated sentence will be one of the four different patterns 1006, 1007, 1008, and 1009. The certain sentence pattern will be completed with the option values. Similarly, for the measurements group 1010, there are three possible sentence patterns 1011, 1012, and 1013. No sentence will be generated for this group if all the measurements values are all none as 1014. For the mass effect group 1020, there are two possible sentence patterns 1021 and 1022. No sentence is generated if no mass effect option is selected as 1023. By following this converting method and predefined sentence patterns, all the filled templates of the study are automatically parsed and converted into readable sentences.

The following two examples show how a set of one or more entry option pairs can be mapped into a sentence using a rule as demonstrated in FIG. 10. Although the sentences are in English, the report generation software 120 can preferably generate the sentences in a variety of other spoken languages:

Example 1

Selected anatomy: left frontal lobe
Diagnosis: parenchymal bleed
Size: medium
Acuity: acute
Sentence: Medium acute parenchymal bleeding in the left frontal lobe.

Example 2

Selected anatomy: right frontal lobe
Diagnosis: parenchymal bleed
With edema: True
Sentence: Parenchymal bleeding with surrounding edema in the right frontal lobe.

Referring to FIG. 11, an interactive window 1100 shows the generated medical report. For the ease of illustration, the report is generated from only one filled template. The head section of the report 1101 is automatically filled by parsing from the metadata of the image. The descriptions of findings part 1102 is automatically filled with sentences parsed from filled templates. In addition, the placement of sentences in different categories is determined by the anatomy of the finding. In this example, the sentences 1103 are placed in the Brain category, because the anatomy of the filled template is the right frontal lobe, which belongs to the brain. The rest of categories in part 1102 are filled with default values, since no findings that related to them are entered in this example. The Impression 1104 of the report is intended to include all the important and major findings in the study concisely. The system adds the findings from templates whose Impression option 680 (FIG. 6) set to yes. The physician can edit or confirm the report.

Use of Machine Learning to Improve System Performance

In some embodiments, the system may include machine learning software that uses monitored interactions with the system to improve the system's operation. For example, the system may determine that a particular physician, or physicians in general, tend to select a particular template whenever a particular feature is present in a medical image of a particular type, even when this template is presented near the end of the filtered template list. Based on this observation, the system may elevate the position of the template in filtered lists when the feature is present; this may be done on a physician-by-physician basis or for all physician-users of the system.

SUMMARY

The diagnostic reporting system advantageously overcomes several limitations of existing technologies and alternatives. It pre-processes the medical studies, and takes advantage of the computer generated data to enable the fast entering of findings. The system preferably has one built-in template designed for each finding-anatomy pair. Most entries of the templates have predefined options, and in this way, the physician can specify a finding quickly and efficiently. Also, the present system can automatically fill in measurements in the template as the physician measures. Moreover, the system can automatically generate a readable medical report based on the templates filled, which further saves time. In contrast to existing diagnostic systems where physicians speak into a microphone, the system requires less speaking, and avoids medical errors caused by speech recognition errors. Lastly, as electronic medical records become ubiquitous, physicians are expected to enter patient information and findings in a more uniform and standardized way. The system offers a simple but effective solution towards this expectation, because findings are described with built in templates, and reports are generated with predefined formats.

The system disclosed herein may be implemented as a computer system programmed with code modules. The computer system may, in some cases, include multiple distinct computers or computing devices (e.g., physical servers, workstations, storage arrays, tablets, cloud computing resources, etc.) that communicate and interoperate over a network to perform the described functions. Each such computing device typically includes a hardware processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

In view of the many possible embodiments to which the principles of the invention may be applied, it should be recognized that the illustrated embodiment is only a preferred example of the invention and should not be taken as a limitation on the scope of the invention. Accordingly, the disclosed embodiments of the invention are merely illustrative and do not serve to limit the scope of the invention.

What is claimed is:

1. A computer-implemented process for efficiently generating medical reports for medical imaging studies, comprising, by execution of program instructions by a computing system:
   applying anatomical segmentation to an image of a medical imaging study of a patient, wherein applying anatomical segmentation comprises identifying anatomical structures shown in the image, and identifying pixels of the image that correspond to each of the anatomical structures;
   displaying the image on a display;
   detecting user selection of a location of interest in the image;
   in response to the selection, generating and displaying a filtered list of templates corresponding to the selected location, the filtered list of templates generated at least partly by identifying, based on the anatomical segmentation, an anatomical structure corresponding to the selected location, and identifying templates corresponding to the anatomical structure, the anatomical segmentation providing separation of anatomical structures from background or from each other;
   receiving user selection of a template from the filtered list of templates, wherein the selected template comprises a plurality of fields for entry of information regarding a finding associated with the selected location in the image;
   displaying the selected template on the display;
   receiving user input specifying or confirming entries in the fields of the selected template; and
   generating a medical report for the medical imaging study, wherein generating the medical report comprises generating sentences corresponding to entries in the fields of the selected template.

2. The process of claim 1, wherein the filtered list of templates comprises a plurality of templates corresponding to the anatomical structure, each of which corresponds to a different respective finding.

3. The process of claim 1, wherein the template comprises a field for which the user selects one of a plurality of predefined options to create an entry-option pair, and wherein generating the medical report comprises converting the entry-option pair into a textual sentence.

4. The process of claim 1, wherein generating the filtered list of templates comprises identifying a set of one or more anatomical structures falling within a predefined distance of the selected image location, and identifying templates corresponding to the set of one or more anatomical structures.

5. The process of claim 1, wherein generating and displaying the filtered list of templates comprises:
   identifying first and second anatomical structures falling within a predefined distance of the selected image location; and
   displaying a multi-level menu having a first level that lists the first and second anatomical structures, and having a second level that lists, for each of the first and second anatomical structures, a list of templates corresponding to the respective anatomical structure, said templates corresponding to respective findings.

6. The process of claim 1, further comprising:
   generating a predicted diagnosis based on an analysis of the image by the computing system; and
   pre-filling at least one field of the template based on the predicted diagnosis.

7. The process of claim 6, wherein generating and displaying the filtered list of templates further comprises selecting one or more templates that correspond to the predicted diagnosis.

8. The process of claim 7, wherein the filtered list of templates is displayed as a list of finding types, each of which corresponds to a respective template.

9. The process of claim 1, further comprising:
   generating a measurement of a selected region of the image, wherein generating the measurement comprises determining a quantity of pixels corresponding to the selected region; and
   automatically entering the measurement into the template.

10. The process of claim 1, wherein generating the medical report comprises arranging the sentences by anatomical structure.

11. The system of claim 1, wherein the report generation software component is configured to arrange the textual sentences by anatomical structure.

12. A computing system comprising one or more computing devices, the computing system comprising:
   a data repository that stores a plurality of templates for entry of data describing findings associated with medical imaging studies, at least some of the templates corresponding to particular anatomical structures and associated findings;
   a pre-processing software component configured to apply anatomical segmentation to images of the medical imaging studies to identify anatomical structures shown in the images; and
   a finding collecting software component configured to display the images and to collect data describing findings associated with the images, wherein the finding collecting software component is responsive to user selection of a location of interest by generating and displaying a filtered list of templates corresponding to the selected location, said filtered list comprising less than all of the plurality of templates and being generated based at least partly on an anatomical segmentation of the image by the pre-processing software component, the finding collecting software component further responsive to user selection of a template from the filtered list by displaying the selected template and providing user functionality to enter data into fields of the selected template, including by user selection of predefined entry options, the anatomical segmentation providing separation of anatomical structures from background or from each other; and
   a report generation software component configured to generate medical reports from completed templates generated with the finding collecting software component, the report generation software component configured to convert entries in a completed template into textual sentences.

13. The system of claim 12, wherein the selected template comprises a field for which the user selects one of a plurality of predefined options to create an entry-option pair, and wherein the report generation software component is configured to convert the entry-option pair into a sentence.

14. The system of claim 12, wherein the finding collecting software components configured to generate the filtered list of templates at least partly by identifying a set of one or more anatomical structures falling within a predefined distance of the selected location of interest, and by identifying templates corresponding to the set of one or more anatomical structures.

15. The system of claim 12, wherein the finding collecting software component is configured to: identify first and second anatomical structures falling within a predefined distance of the selected location in the image; and
   displaying a multi-level menu having a first level that lists the first and second anatomical structures, and having a second level that lists, for each of the first and second anatomical structures, a list of templates corresponding to the respective anatomical structure, said templates corresponding to respective findings.

16. The system of claim 12, wherein the pre-processing software component is further configured to generate a diagnosis based on an automated analysis of the image, and the finding collecting software component is configured to pre-fill at least one field of the selected template based on the diagnosis.

17. The system of claim 16, wherein the finding collecting software component, in generating the filtered list of templates, is configured to select one or more templates that correspond to the diagnosis.

18. The system of claim 12, wherein the finding collecting software component includes an interactive measurement tool configured to generate a measurement for a selected region of the image, and to automatically enter the measurement into the template.

19. A computer-implemented process for efficiently generating medical reports for medical imaging studies, comprising, by execution of program instructions by a computing system:
   generating a computer-aided diagnosis based on an automated analysis of an image of a medical imaging study, the computer-aided diagnosis corresponding to a particular region of the image;
   applying anatomical segmentation to the image to identify anatomical structures shown in the image, the anatomical segmentation providing separation of anatomical structures from background or from each other;
   generating a filtered list of one or more templates based at least partly on the computer-aided diagnosis, each template in the filtered list corresponding to a respective finding and including fields for entry of data associated with the finding;

in response to user selection of a template from the filtered list, displaying the template with at least one field pre-filled with data based on the computer-aided diagnosis, the template being editable by a user; and after user acceptance of entries in the template, generating a medical report for the medical imaging study, wherein generating the medical report comprises converting the entries in the template into textual sentences.

20. The process of claim 19, wherein the computer-aided diagnosis comprises:
a plurality of findings, and wherein the filtered list of templates comprises a different respective template for each of the plurality of findings.

21. The process of claim 19, further comprising:
identifying an anatomical structure corresponding to the computer-aided diagnosis; and
displaying the filtered list of templates in response to user selection of an image location corresponding to the anatomical structure.

22. The process of claim 19, wherein the template comprises a field for which
the user selects one of a plurality of predefined options to create an entry-option pair, and wherein generating the medical report comprises converting the entry-option pair into a sentence.

23. A computing system comprising one or more computing devices, the computing system comprising:
a data repository that stores a plurality of templates for entry of data describing findings associated with medical imaging studies, at least some of the templates corresponding to particular anatomical structures and associated findings;
a pre-processing software component configured to generate a computer-aided diagnosis based on an automated analysis of at least one image of a medical imaging study, the computer-aided diagnosis corresponding to a particular region of the image;
a finding collecting software component configured to generate and display a filtered list of one or more templates based at least partly on the computer-aided diagnosis, each template in the filtered list corresponding to a respective finding and including fields for entry of data associated with the finding, wherein the finding collecting software component is responsive to user selection of a template from the filtered list by displaying the template with at least one field pre-filled with data based on the computer-aided diagnosis, and by providing user functionality to edit and confirm entries in the template; and a medical report generation software component configured to generate medical reports from competed templates generated with the finding collecting software component, the report generation software component configured to convert entries in a completed template into textual sentences.

24. The system of claim 23, wherein the filtered list of templates corresponds to a particular anatomical structure and comprises a different respective template for each of a plurality of findings associated with the particular anatomical structure.

25. The system of claim 23, wherein the finding collecting software component includes an interactive measurement tool configured to generate a measurement for a selected region of the image, and to automatically enter the measurement into the template.

26. The system of claim 23, wherein the template comprises a field for which a user selects one of a plurality of predefined options to create an entry-option pair, and the medical report generation software component is configured to convert the entry-option pair into a sentence.

27. The system of claim 26, wherein the medical report generation software component is configured to convert the entry-option pair into a sentence in each of a plurality of languages.

28. The system of claim 23, wherein the pre-processing software component is additionally configured to generate anatomical segmentations of the images, and the finding collecting software component is configured to use the anatomical segmentations to map image locations to filtered lists of templates to display.

* * * * *